United States Patent
Murakami et al.

(10) Patent No.: US 9,901,291 B2
(45) Date of Patent: Feb. 27, 2018

(54) ACTIVITY METER AND SLEEP/AWAKE STATE RECORDING SYSTEM

(71) Applicant: TDK Corporation, Minato-ku (JP)

(72) Inventors: Tomoko Murakami, Shinagawa (JP); Hiromi Sakata, Suginami (JP)

(73) Assignee: TDK Corporation, Minato-ku (JP)

( * ) Notice: Subject to any disclaimer, the term of this patent is extended or adjusted under 35 U.S.C. 154(b) by 118 days.

(21) Appl. No.: 14/800,071

(22) Filed: Jul. 15, 2015

(65) Prior Publication Data

US 2016/0045141 A1    Feb. 18, 2016

(30) Foreign Application Priority Data

Aug. 14, 2014  (JP) ................. 2014-165262

(51) Int. Cl.
| | | |
|---|---|---|
| *G08B 23/00* | (2006.01) | |
| *A61B 5/11* | (2006.01) | |
| *A61B 5/00* | (2006.01) | |
| *G01P 15/08* | (2006.01) | |
| *G01P 15/18* | (2013.01) | |

(52) U.S. Cl.
CPC .......... *A61B 5/1118* (2013.01); *A61B 5/4809* (2013.01); *A61B 5/681* (2013.01); *G01P 15/0891* (2013.01); *G01P 15/18* (2013.01)

(58) Field of Classification Search
CPC . A61B 2562/0219; A61B 5/681; A61B 5/002; A61B 5/14532; A61B 5/1118; A61B 5/11; A61B 5/22; A61B 5/4809; A61B 5/721; A61B 2560/0242; A61B 5/02416; A61B 5/02438; A61B 5/1117; A61B 5/1123

USPC ..... 340/575, 573.1, 572.1, 582, 588, 636.11, 340/686.6, 691.6, 3.43, 991–994

See application file for complete search history.

(56) References Cited

U.S. PATENT DOCUMENTS

| | | | | |
|---|---|---|---|---|
| 6,397,151 B1 * | 5/2002 | Yamagishi | ............. | A63B 24/00 463/8 |
| 8,078,269 B2 * | 12/2011 | Suzuki | ............... | A61B 5/02438 600/509 |

(Continued)

FOREIGN PATENT DOCUMENTS

| | | |
|---|---|---|
| EP | 2 027 815 A2 | 2/2009 |
| JP | 4185846 B2 | 11/2008 |

(Continued)

OTHER PUBLICATIONS

Combined Taiwanese Office Action and Search Report dated Mar. 21, 2016 in Patent Application No. 104119090 (with English language translation of categories of cited documents).

*Primary Examiner* — Daniel Previl
(74) *Attorney, Agent, or Firm* — Oblon, McClelland, Maier & Neustadt, L.L.P.

(57) ABSTRACT

According to an embodiment, an activity meter includes an acceleration sensor configured to detect acceleration in at least one axis direction, an acceleration energy detection section configured to detect acceleration energy based on an acceleration signal of the acceleration sensor and a control section. The control section determines removal of the activity meter from a target person based on acceleration energy detected by the acceleration energy detection section and an acceleration component in a direction of gravity in the acceleration signal of the acceleration sensor.

4 Claims, 9 Drawing Sheets

(56) References Cited

U.S. PATENT DOCUMENTS

| | | | |
|---|---|---|---|
| 2008/0139952 A1* | 6/2008 | Kuroda | A61B 5/02438 600/508 |
| 2009/0182239 A1* | 7/2009 | Ouchi | A61B 5/02433 600/500 |
| 2010/0130258 A1* | 5/2010 | Fujiwara | G01V 7/04 455/566 |
| 2015/0168365 A1* | 6/2015 | Connor | G01N 33/02 356/51 |
| 2015/0370597 A1* | 12/2015 | Faaborg | G06F 9/46 718/102 |

FOREIGN PATENT DOCUMENTS

| | | |
|---|---|---|
| JP | 5263774 B2 | 8/2013 |
| TW | 201306793 A1 | 2/2013 |
| TW | 201324444 A1 | 6/2013 |

\* cited by examiner

| DATE | TIME | ESTIMATION RESULT |
|---|---|---|
| 2014/08/08 | 08:55:01 | AWAKE |
| 2014/08/08 | 08:55:02 | AWAKE |
| 2014/08/08 | 08:55:03 | AWAKE |
| ⋮ | ⋮ | ⋮ |
| 2014/08/08 | 21:30:21 | AWAKE |
| 2014/08/08 | 21:30:22 | ASLEEP |
| 2014/08/08 | 21:30:23 | ASLEEP |
| ⋮ | ⋮ | ⋮ |

# ACTIVITY METER AND SLEEP/AWAKE STATE RECORDING SYSTEM

CROSS-REFERENCE TO RELATED APPLICATION

This application is based upon and claims the benefit of priority from the prior Japanese Patent Application No. 2014-165262 filed in Japan on Aug. 14, 2014; the entire contents of which are incorporated herein by reference.

FIELD

An embodiment described herein relates generally to an activity meter and a sleep/awake state recording system.

BACKGROUND

There are proposals of systems configured to determine a human activity status or the like. For example, there is a system configured to attach an apparatus provided with an acceleration sensor to a target person whose activity status is determined and determine whether the target person is in a sleep state or an awake state based on an output of the acceleration sensor.

When a user who is a target person whose activity status is determined wears the apparatus on his/her arm, it is automatically determined whether the user is in a sleep state or an awake state from the output of the acceleration sensor. When such an activity meter of a type wearable on the user's body is attached to the body, it is possible to automatically determine whether the user is in a sleep state or an awake state.

However, the user may remove the activity meter from his/her body. When the user removes the activity meter from, for example, his/her arm and leaves the activity meter unattached, the activity meter is placed in an immobile or still state, resulting in a problem that the activity meter misjudges that the user is in a sleep state.

DETAILED DESCRIPTION

An activity meter of an embodiment is an activity meter attachable to a target person whose activity amount is measured, including an acceleration sensor configured to detect acceleration in at least one axis direction, an acceleration energy detection section configured to detect acceleration energy based on an acceleration signal of the acceleration sensor, and a removal determining section configured to determine removal of the activity meter from the target person based on the acceleration energy detected by the acceleration energy detection section and an acceleration component in a direction of gravity in the acceleration signal of the acceleration sensor.

An activity meter of the embodiment is an activity meter attachable to a target person whose activity amount is measured, including an acceleration sensor configured to detect accelerations in at least three axis directions, an acceleration energy detection section configured to detect acceleration energy based on an acceleration signal of the acceleration sensor, and a removal determining section configured to determine removal (unattached state) of the activity meter from the target person based on the acceleration energy detected by the acceleration energy detection section and an acceleration component in a direction of gravity in the acceleration signal of the acceleration sensor.

A sleep/awake state recording system of the embodiment is a sleep/awake state recording system made up of an activity meter attachable to a target person whose activity amount is measured and a terminal communicable with the activity meter, in which the activity meter includes an acceleration sensor configured to detect acceleration in at least one axis direction, an acceleration energy detection section configured to detect acceleration energy based on an acceleration signal of the acceleration sensor, a removal determining section configured to determine removal of the activity meter from the target person based on the acceleration energy detected by the acceleration energy detection section and an acceleration component in a direction of gravity in the acceleration signal of the acceleration sensor, an awake state determining section configured to determine whether the target person is in an awake state or not based on a level of smoothness of the acceleration component in the direction of gravity in the acceleration signal of the acceleration sensor and the acceleration energy, a sleep state determining section configured to determine, except when the target person is determined to be in the awake state, that the target person is in a sleep state, a sleep/awake state storage section configured to record information on the sleep state and the awake state, and an information transmitting section configured to transmit information on the sleep state and the awake state stored in the sleep/awake state storage section, and the terminal includes a correction section configured to correct the information on the sleep state and the awake state received from the activity meter and a storage section configured to store the corrected information.

Hereinafter, an embodiment will be described with reference to the accompanying drawings.

(Configuration)

Figure 1:
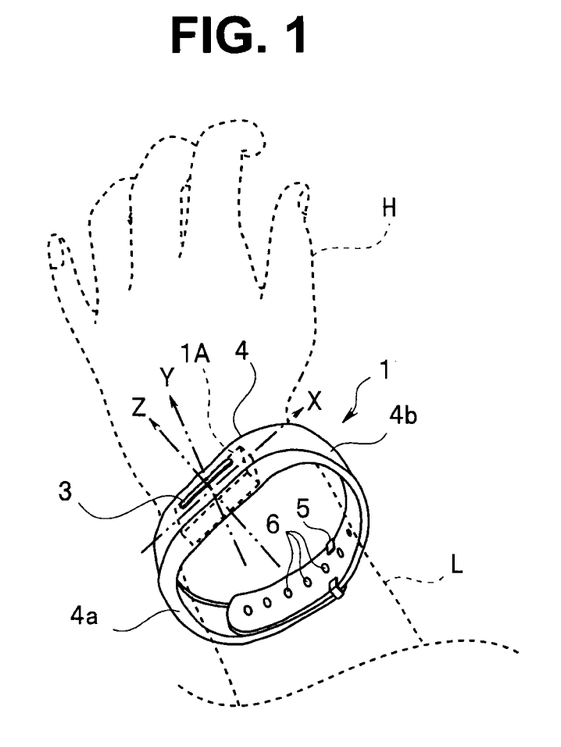
FIG. 1 is an outline view of a wristband-type activity meter 1 according to an embodiment.
Figure 2:
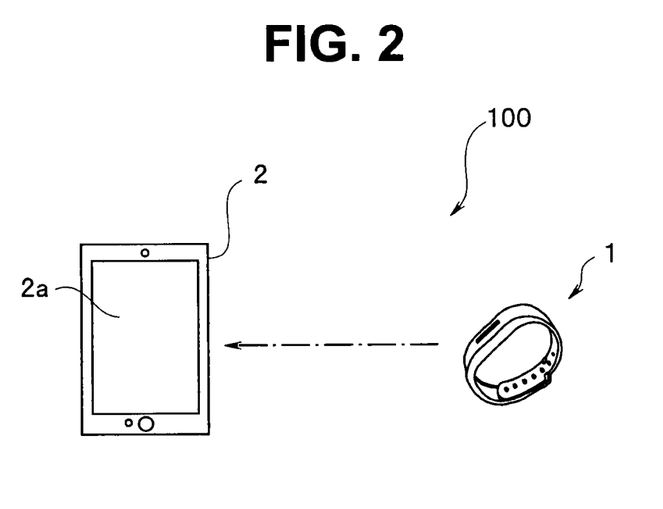
FIG. 2 is a configuration diagram of a sleep/awake state recording system 100 made up of the wristband-type activity meter and a smartphone according to the embodiment.

FIG. 1 is an outline view of a wristband-type activity meter 1 according to an embodiment. FIG. 2 is a configuration diagram of a sleep/awake state recording system 100 made up of the wristband-type activity meter and a smartphone.

The activity meter 1 wearable on a target person whose activity amount is measured is a wristband-type device capable of recording an activity amount of the user who is the target person and transmitting the activity amount to a smartphone 2.

The activity meter 1 is a band-shaped wristband type to be worn by being wrapped around the user's arm (shown by a dotted line) L and an elongated operation button 3 is provided in a center thereof. The operation button 3 is operated when making various settings or the like.

The activity meter 1 includes two extended portions 4a and 4b that extend from both sides of a central portion of a band 4 on which the operation button 3 or the like is arranged. A clasp 5 is provided at an end portion of the extended portion 4a and a plurality of holes 6 into which a protruding portion (not shown) of the clasp 5 is fitted are formed in the extended portion 4b at a predetermined interval. The user can wear the activity meter 1 on the arm L by fitting the protruding portion (not shown) formed in the clasp 5 into the hole 6 at an arbitrary position.

The operation button 3 is disposed in the activity meter 1 so as to come to the front side which is opposite to the back side face of the activity meter 1 in close contact with the arm L when the user wears the activity meter 1 on the arm L.

The sleep/awake state recording system 100 shown in FIG. 2 is a sleep/awake state recording system using the activity meter 1.

As will be described later, the activity meter 1 has a radio communication function and can transmit state information on a sleep state and an awake state which will be described later to the smartphone 2. The user can transmit data of the state information on the sleep state and the awake state recorded in the activity meter 1 to the smartphone 2, store the data in a memory of the smartphone 2, and manage the data according to an application program stored in the smartphone 2 or display the data on a display section 2a of the smartphone 2.

Note that the activity meter 1 has an acceleration sensor, generates, records or transmits activity data such as the user's activity amount and count of steps from the output of the acceleration sensor. Here, description of recording and transmission of such data is omitted and a sleep/awake state determination transmission process which is one of the functions of the activity meter 1 will be described.

Figure 3:
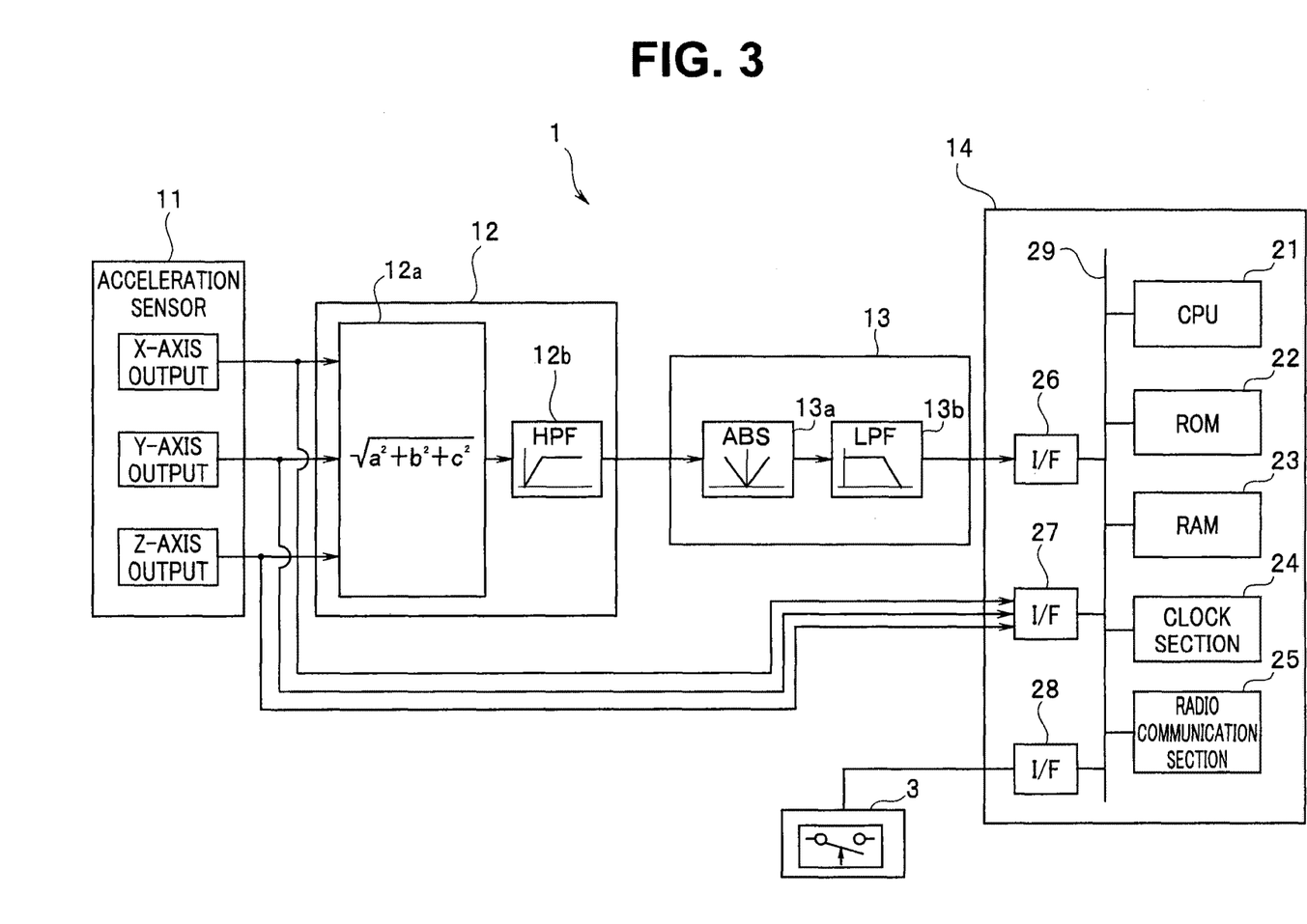
FIG. 3 is a block diagram illustrating a configuration of the activity meter 1 of the embodiment.

FIG. 3 is a block diagram illustrating a configuration of the activity meter 1 of the present embodiment.

The activity meter 1 has a main unit 1A including an operation button 3, an acceleration sensor 11, an acceleration detection section 12, an acceleration energy detection section 13 and a control section 14. In FIG. 1, as shown by a dotted line, the main unit 1A is detachably attached to a central portion of the band 4.

The activity meter 1 has an activity amount measuring function, a sleep state and awake state determining function which will be described later, a function of recording and transmitting the measured activity amount and a function of recording and transmitting state information on the determined sleep state and awake state.

The acceleration sensor 11 is a three-axis acceleration sensor which includes three sensors so as to be able to detect accelerations in three axis (X-axis, Y-axis and Z-axis) directions orthogonal to each other and outputs X-axis output, Y-axis output and Z-axis output as acceleration signals of the respective axes. Each output of the acceleration sensor 11 configured to detect accelerations in at least three axis directions is inputted to the acceleration detection section 12 and the control section 14.

As shown in FIG. 1, when the activity meter 1 is worn on the user's arm L, the user can wear the activity meter 1 on the arm L so that the X-axis direction is parallel to a back of a hand H and orthogonal to an axis of the arm L, the Y-axis direction is parallel to the back of the hand H and parallel to the axis of the arm L, and the Z-axis direction is orthogonal to the back of the hand H. In FIG. 1, the arm L is passed through the ring-shaped band 4 of the activity meter 1 so that the arm L is oriented from the front toward the back of the sheet.

The acceleration detection section 12 includes a square root of sum of squares calculation section 12a and a high pass filter (HPF) 12b.

The square root of sum of squares calculation section 12a is a circuit configured to generate a signal of the square root of sum of squares of each output of the acceleration sensor 11. Here, since accelerations in a plurality of directions (here, three directions) are used, the square root of sum of squares calculation section 12a configured to generate a signal of the square root of sum of squares of each output is used, but a sum of squares calculation circuit configured to generate a signal of sum of squares may be used instead of the square root of sum of squares calculation section 12a.

The high pass filter 12b is an offset canceller circuit configured to remove gravity acceleration from the output of the square root of sum of squares calculation section 12a.

Note that the acceleration sensor 11 is a three-axis acceleration sensor here, but the acceleration sensor 11 may also be a 4- or more-axis acceleration sensor.

Thus, the acceleration detection section 12 detects acceleration from the output of the acceleration sensor 11 and outputs an acceleration signal. The acceleration signal outputted from the acceleration detection section 12 is inputted to the acceleration energy detection section 13.

The acceleration energy detection section 13 includes an absolute value circuit 13a and a low pass filter 13b, and detects acceleration energy based on the acceleration signal of the acceleration sensor 11.

The acceleration signal inputted to the acceleration energy detection section 13 is inputted to the absolute value circuit 13a. The absolute value circuit 13a calculates an absolute value of the inputted acceleration signal and outputs the absolute value to the low pass filter 13b.

The low pass filter 13b averages the output of the absolute value circuit 13a, detects an intensity of acceleration and outputs the intensity to the control section 14. Thus, the acceleration energy detection section 13 constitutes an acceleration intensity detection section configured to detect an intensity of acceleration from the acceleration signal from the acceleration detection section 12.

The control section 14 includes a central processing unit (hereinafter referred to as "CPU") 21, a ROM 22, a RAM 23, a clock section 24, a radio communication section 25 and interfaces (hereinafter abbreviated as "I/F") 26, 27 and 28, which are connected to each other via a bus 29.

The CPU 21 can acquire the output of the acceleration energy detection section 13 via the I/F 26.

Similarly, the CPU 21 can acquire an X-axis output, Y-axis output and Z-axis output of the acceleration sensor 11 via the I/F 27.

Furthermore, the CPU 21 can acquire an operating state of the operation button 3 via the I/F 28.

The ROM 22 of the control section 14 stores an awake/sleep state determining processing program which will be described later. Note that the ROM 22 may also be a rewritable non-volatile memory such as a flash memory.

The clock section 24 is a circuit configured to generate and output time information, and the CPU 21 can acquire information on dates and times from the clock section 24.

The radio communication section 25 is a circuit configured to carry out data communication with the smartphone 2 and is a circuit configured to carry out short-distance radio communication.

The activity meter 1 has the above-described configuration and is worn on the user's arm, and can determine whether the user is in a sleep state or an awake state, record and transmit the determination result to the smartphone 2.

(Operation)

A sleep/awake state determination process will be described.

Figure 4:
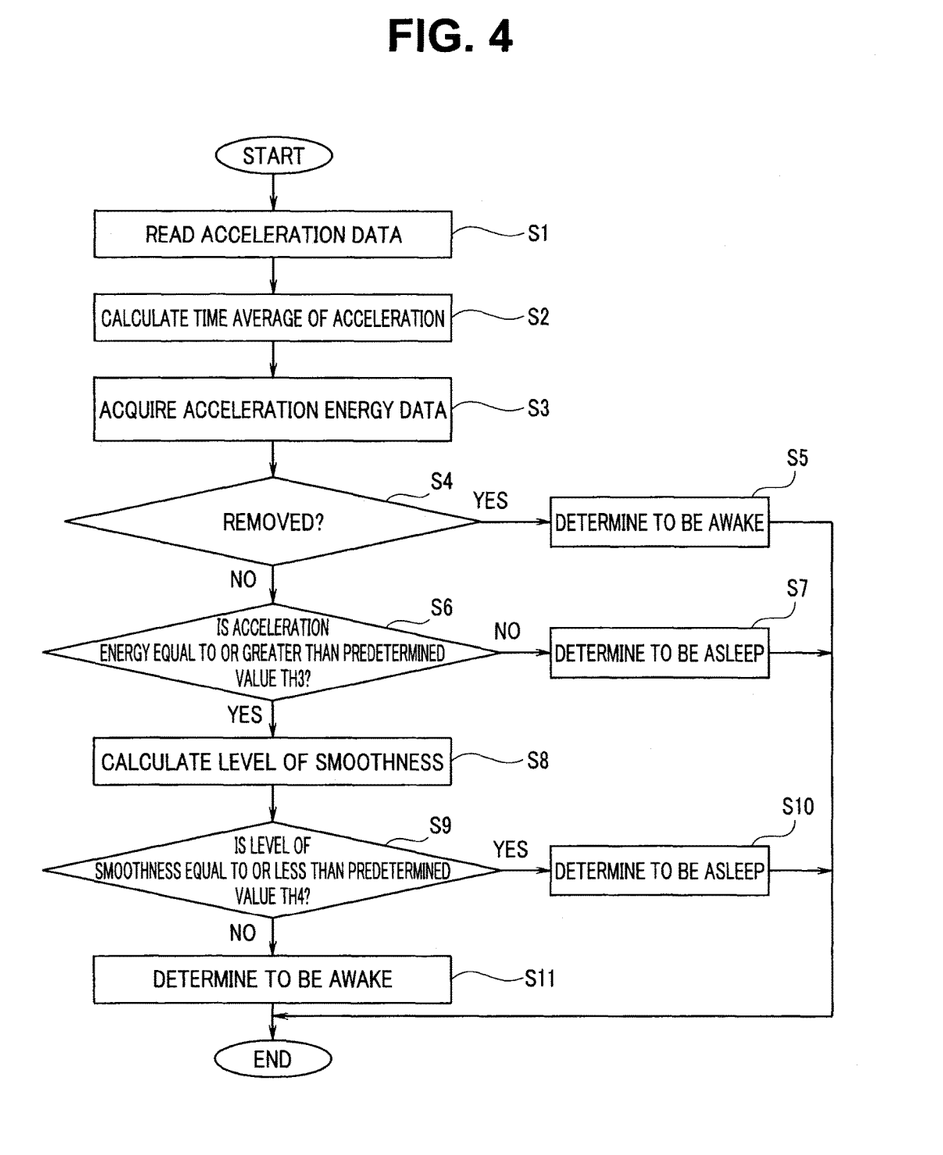
FIG. 4 is a flowchart illustrating a flow example of a sleep/awake state determination process according to the embodiment.

FIG. 4 is a flowchart illustrating a flow example of the sleep/awake state determination process. A sleep/awake state determination is made by the CPU 21 reading the sleep/awake state determination processing program from the ROM 22 and developing and executing the program on the RAM 23. For example, when a sleep/awake information acquisition mode is set, the sleep/awake state determination processing program is executed. The process in FIG. 4 is executed in a predetermined cycle, for example, in one-second cycle.

The CPU 21 reads the acceleration data inputted in a predetermined cycle (S1). Here, respective acceleration signals in the X-, Y- and Z-axis directions of the acceleration sensor 11 are sampled at predetermined sampling timing, for example, at timing of several tens of times per second and inputted to the CPU 21 and stored in the RAM 23.

The CPU 21 calculates a time average of respective accelerations in the X-, Y-, Z-axis directions (S2). That is, to remove a noise component, the CPU 21 calculates an average value for a predetermined time, for example, an average value of data for several seconds for read value data of the respective acceleration signals in the X-, Y-, Z-axis directions.

Furthermore, the CPU 21 acquires data of acceleration energy AE from the output of acceleration energy detection section 13 (S3).

Next, the CPU 21 determines whether the user removes the activity meter 1 form the arm or not (S4).

The determination in S4 is made based on whether the acceleration energy AE is equal to or less than a predetermined value TH1 and whether an absolute value |Ya| of the Y-axis acceleration Ya which is a time average value of the acceleration signal in the Y-axis direction exceeds a predetermined value TH2 or not. That is, it is determined whether the activity meter 1 is removed from the arm depending on whether the following expression (1) holds or not. The predetermined value TH1 is an extremely small value and is a value at a level that it is possible to detect that the activity meter 1 is at rest. The predetermined value TH2 is a large value among output levels of the Y-axis acceleration Ya and the largest value is a value detected when the Y-axis direction matches the direction of gravity when the activity meter 1 is at rest.

$$(AE \leq TH1) \text{ and } (|Ya| > TH2) \quad (1)$$

When the above expression (1) holds, it is determined that the user is awake.

This is because in addition to the fact that the user's activity amount is extremely small, with acceleration energy AE being equal to or less than the predetermined value TH1, the magnitude of acceleration in the direction of gravity, the Y-axis direction here, exceeds the predetermined value TH2, and it is thereby possible to estimate that the activity meter 1 is placed on, for example, a desk.

Figure 5:
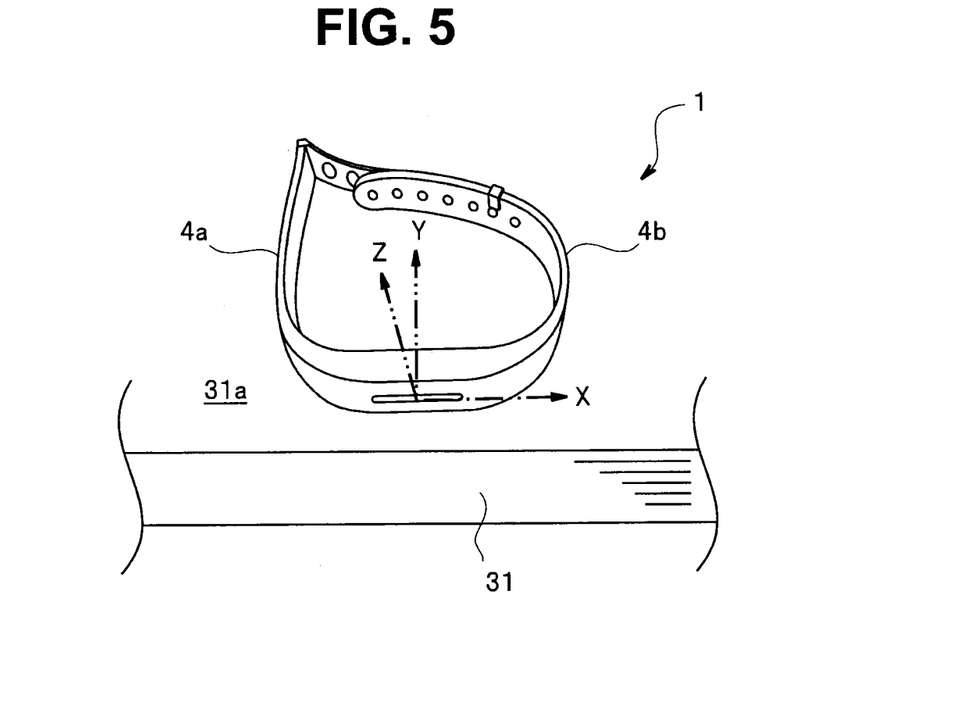
FIG. 5 is a perspective view illustrating XYZ-axis directions when the activity meter 1 according to the embodiment is placed on a table surface 31a of a table 31.
Figure 6:
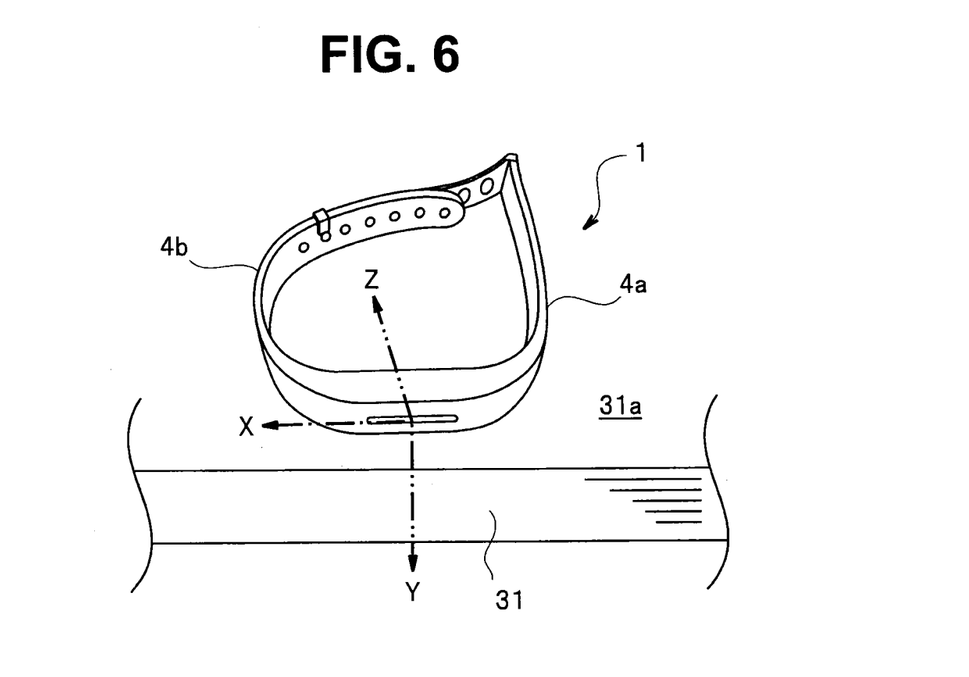
FIG. 6 is a perspective view illustrating XYZ-axis directions when the activity meter 1 in the state in FIG. 5 is turned over and placed on the table surface 31a of the table 31.

FIG. 5 is a perspective view illustrating the XYZ-axis directions when the activity meter 1 is placed on a table surface 31a of a table 31. FIG. 6 is a perspective view illustrating the XYZ-axis directions when the activity meter 1 in FIG. 5 is turned over and the activity meter 1 is placed on the table surface 31a of the table 31.

As shown in FIG. 5 and FIG. 6, when placed on a flat surface such as the table surface 31a of the table 31, the Y-axis direction of the band-type activity meter 1 becomes orthogonal to the table surface 31a. For this reason, when the activity meter 1 is removed from the user's arm and left unattached on the table 31 or the like, the acceleration Ya in the Y-axis direction, that is, the direction of gravity increases.

Since the activity meter 1 is removed from the user's arm, the acceleration energy AE is small and the absolute value of acceleration in the direction of gravity increases.

Note that an example has been described in FIG. 5 and FIG. 6 where the Y-axis direction is orthogonal to the table surface 31a, but without being limited to this, for example, the Z-axis direction becomes orthogonal to the table surface 31a when, for example, the activity meter 1 is placed such that the operation button 3 comes into contact with the table surface 31a. In this case, the acceleration Za in the Z-axis direction increases.

As described above, the process in S4 constitutes a removal determining section configured to determine removal of the activity meter 1 from the user, that is, an unattached state, based on the acceleration energy AE detected by the acceleration energy detection section 13 and an acceleration component in the direction of gravity in the acceleration signal of the acceleration sensor 11. In the process in S4, when the acceleration energy AE is equal to or less than the predetermined value TH1 and the acceleration component in the direction of gravity is equal to or greater than the predetermined value TH2, it is determined that the activity meter 1 is removed from the user.

Thus, as a result of the determination in S4, when it is determined that the user removes the activity meter 1 from the arm (S4: YES), the CPU 21 determines that the user removes the activity meter 1 from the arm and is in an awake state (S5).

When it is determined that the user does not remove the activity meter 1 from the arm (S4: NO), the CPU 21 determines whether the acceleration energy AE is equal to or greater than a predetermined value TH3 (S6).

When the acceleration energy AE is not equal to or greater than the predetermined value TH3 (S6: NO), the CPU 21 determines that the user is in a sleep state (S7). That is, although the user wears the activity meter 1 on the arm, the acceleration energy AE is small, and so it is determined that the user is in a sleep state.

When the acceleration energy AE is equal to or greater than the predetermined value TH3 (S6: YES), the CPU 21 calculates a level of smoothness of the value of the acceleration energy AE (S8).

Here, the level of smoothness FL(i) defined in the following expression (2) is calculated.

$$FL(i) = \left(\sum_{k=1}^{m} AE[i] - AE(i-k)\right) + \left(\sum_{k=1}^{m} AE[i] - AE(i+k)\right) \quad (2)$$

Here, FL(i) is the level of smoothness at a time i.

More specifically, FL(i) in expression (2) is the sum total of a first sum of a difference between each of m (m is an integer) portions of acceleration energy up to an mth portion before acceleration energy AE(i) at a time i and the acceleration energy AE(i) at the time i, and a second sum of a difference between each of the m (m is an integer) portions of acceleration energy up to the mth portion after the acceleration energy AE(i) at the time i.

Note that although the level of smoothness is calculated according to the calculation expression defined in expression (2) here, the level of smoothness may be calculated by other means such as calculating the level of smoothness from the sum of a difference between each of m (m is an integer) portions of acceleration energy up to the mth portion before acceleration energy AE(i) at the time i and the acceleration energy AE(i) at the time i.

After S8, the CPU 21 determines whether the level of smoothness is equal to or less than a predetermined value TH4 or not (S9). The fact that the level of smoothness in expression (2) is equal to or less than the predetermined value TH4 means that the acceleration energy values are substantially constant when these values are time-sequentially arranged in a graph and that the level of smoothness of the values of the acceleration energy AE is high. Thus, the value of the predetermined value TH4 is an extremely small value. The predetermined value TH4 is an extremely small value and is a value at a level that the acceleration energy AE can be considered substantially invariable.

When the level of smoothness is equal to or less than the predetermined value TH4 (S9: YES), that is, when the change in the acceleration energy value is small, the CPU 21 determines that the user is in a sleep state (S10). The fact that the level of smoothness FL(i) which is the sum total of the first sum and the second sum is small in S9 means that the acceleration energy AE is equal to or greater than the predetermined value TR3, but does not substantially change, that is, a constant state in which accelerations in the X-axis, Y-axis and Z-axis directions do not change, and so it is determined that the user is in a sleep state.

When the acceleration energy AE is large because the body motion when the user is asleep is large, the processes in S8 and S9 prevent the activity meter 1 from misjudging that the user is awake.

When the level of smoothness is not equal to or less than the predetermined value TH4 (S9: NO), the CPU 21 determines that the user is in an awake state (S11). That is, the fact that the level of smoothness FL(i) which is the sum total of the first sum and the second sum is not small means that the acceleration energy AE is large and changing a great deal, that is, the state is not a constant state in which accelerations in the X-axis, Y-axis and Z-axis directions are not changing, and so the user is determined to be in an awake state.

Figure 7:
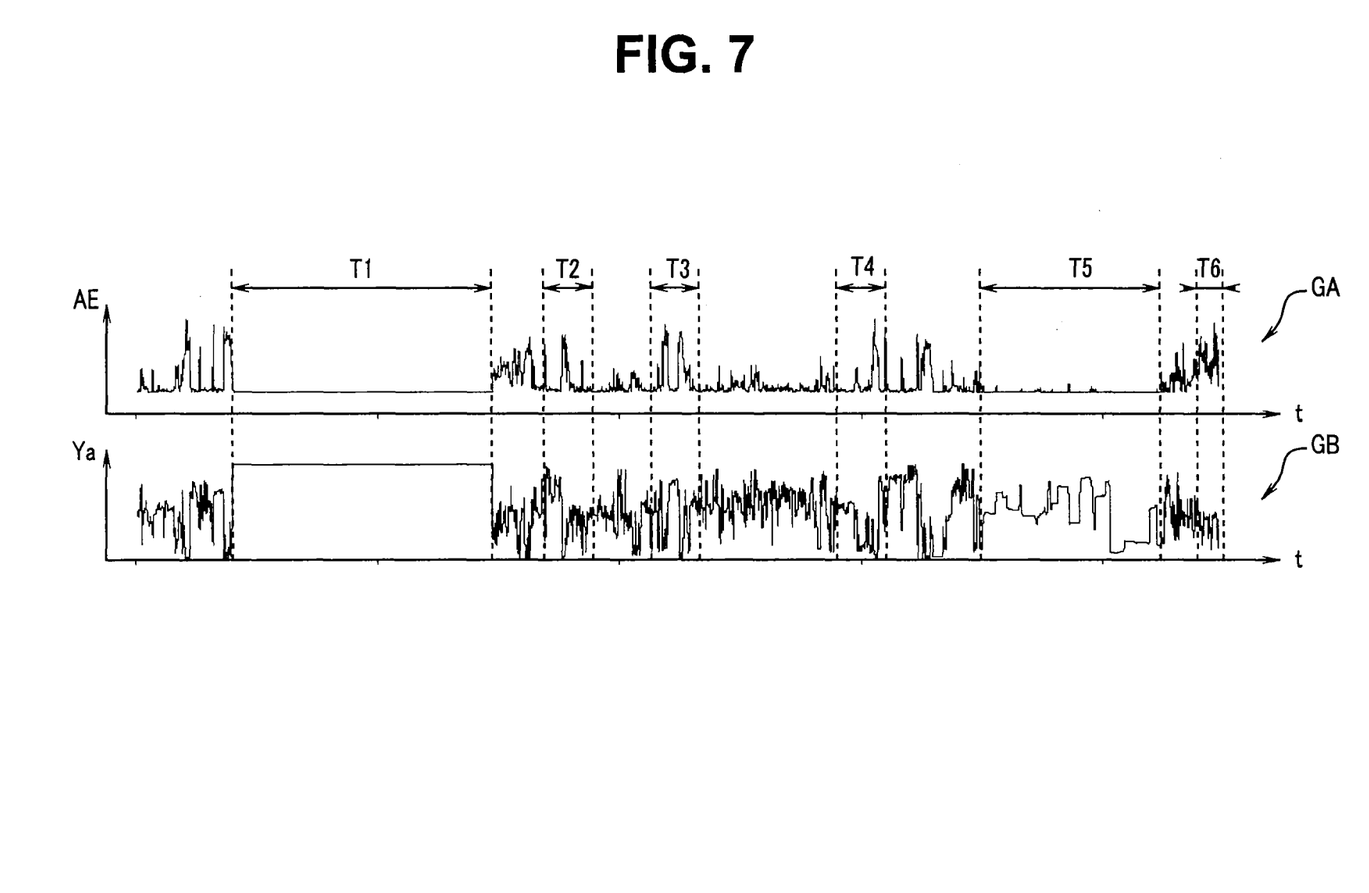
FIG. 7 is a graph illustrating output states of acceleration energy and Y-axis direction acceleration according to the embodiment.

FIG. 7 is a graph illustrating output states of acceleration energy and Y-axis direction acceleration. In the graph in FIG. 7, the horizontal axis denotes a time t and indicates changes in the acceleration energy AE and the Y-axis direction acceleration Ya over time actually measured with the activity meter 1 worn on a certain examinee's arm.

A graph GA on the top row of FIG. 7 is a graph of values of the acceleration energy AE and a graph GB on the bottom row of FIG. 7 is a graph of values of the Y-axis direction acceleration Ya.

In FIG. 7, a period T1 is a period while the examinee removes the activity meter 1 from the arm, a period T2 is a commuting time period, a period T3 is a period while the examinee is out, a period T4 is a commuting time period, a period T5 is a sleeping time period and a period T6 is a commuting time period. During the period T1, the acceleration energy AE has a small value and the Y-axis direction acceleration Ya has a large value. In contrast, during the period T5, the acceleration energy AE has a small value, but the Y-axis direction acceleration Ya of a time average has a smaller value than that during the period T1 and fluctuates.

According to the aforementioned process in S4, since the examinee is not in a sleep state and the activity meter 1 is removed from the arm and left unattached during the period T1, it is possible to determine that the user is awake.

Figure 8:
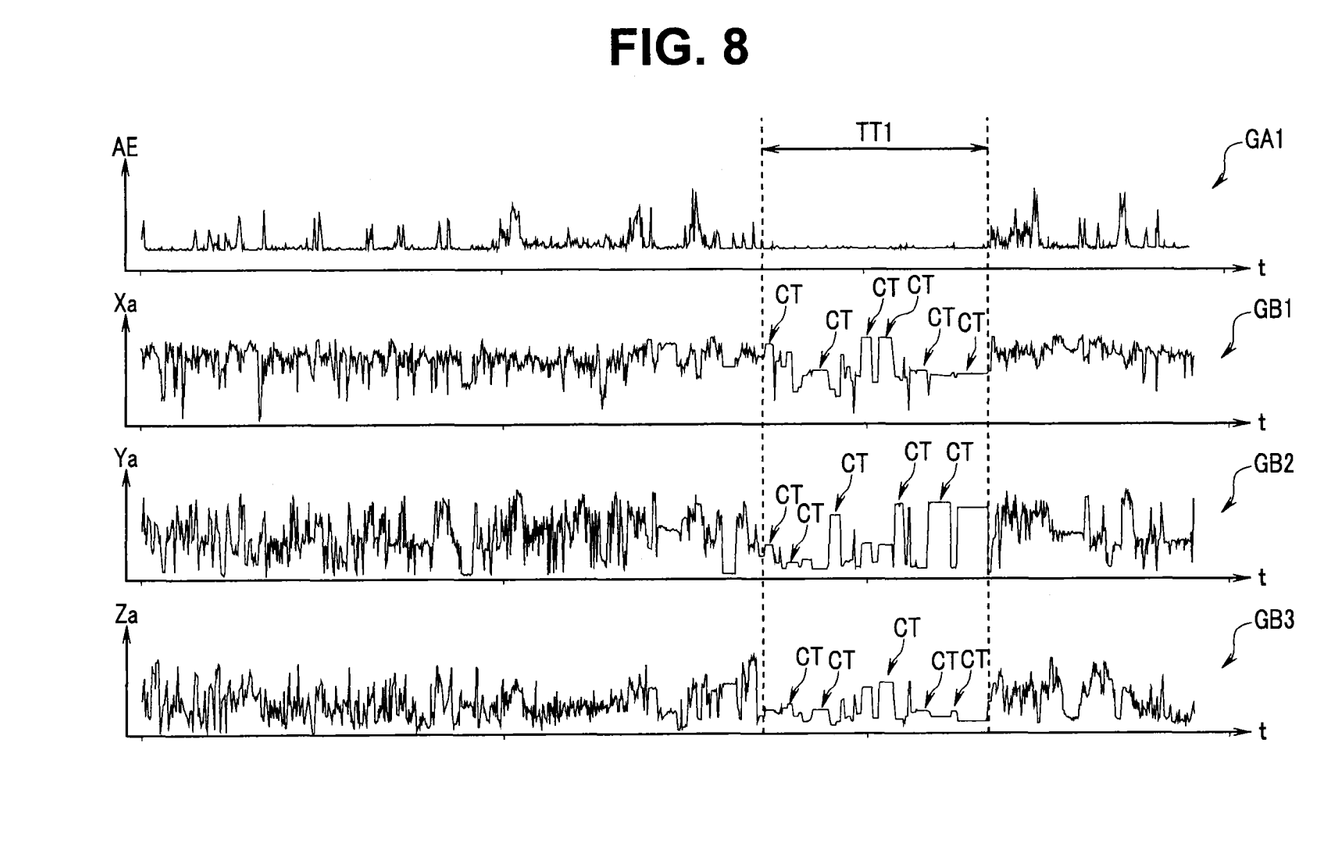
FIG. 8 is a graph illustrating output states of acceleration energy and accelerations in three X-, Y- and Z-axis directions according to the embodiment.

FIG. 8 is a graph illustrating output states of acceleration energy and accelerations in the three X-, Y- and Z-axis directions. In the graph in FIG. 8, the horizontal axis denotes a time t showing changes in the acceleration energy AE and accelerations Xa, Ya and Za in the three X-, Y- and Z-axis directions over time on one day actually measured with the activity meter 1 worn on the examinee's arm.

A graph GA1 on the top row in FIG. 8 is a graph showing acceleration energy AE values, a graph GB1 on the second row in FIG. 8 is a graph showing X-axis direction acceleration Xa values, a graph GB2 on the third row in FIG. 8 is a graph showing Y-axis direction acceleration Ya values and a graph GB3 on the bottom row in FIG. 8 is a graph showing Z-axis direction acceleration Za values.

In FIG. 8, a period TT1 is a time period while the examinee is asleep.

Since the state in which the examinee is immobile continues within the period TT1 as shown in FIG. 8, there are a plurality of periods during which acceleration values in the X, Y and Z axes are constant. In the graph GB1 in FIG. 8, the period CT shows a period during which acceleration values do not change and remain constant during the period TT1. In the graphs GB2 and GB3, there are also a plurality of periods during which acceleration values are constant. Since the user remains immobile after tossing and turning in bed, the acceleration values in the X, Y and Z axes become constant before and after tossing and turning, and the graphs GB1, GB2 and GB3 during the period TT1 show stepped waveforms as shown in FIG. 8.

Since the acceleration values do not change and are constant in the respective X-axis direction, Y-axis direction and Z-axis direction as well, the graph GA1 during the period TT1 becomes substantially flat.

When the acceleration energy AE value is equal to or greater than the predetermined value TH3, the aforementioned levels of smoothness in S8 and S9 are processes to determine whether such a graph GA1 is flat or not. When the level of smoothness calculated in S8 is small, that is, when the graph GA1 is flat, the CPU 21 determines that the user is in a sleep state (S10), and does not make erroneous determinations that the user is in an awake state.

Conversely, when the level of smoothness calculated in S8 is not small, that is, when the graph GA1 is not flat, the CPU 21 can determine that the user is in an awake state (S11). As described above, it is determined, based on the acceleration energy AE value and the level of smoothness of the acceleration energy AE, whether the user is in a sleep state or in an awake state.

As described above, the processes in S8, S9 and S11 constitute an awake state determining section configured to determine whether the user is in an awake state or not based on the level of smoothness of the acceleration component in the direction of gravity and the acceleration energy AE in the acceleration signal of the acceleration sensor 11. The level of smoothness is defined by whether the change in the acceleration energy AE value falls within a predetermined value or not. When the acceleration energy AE is equal to or greater than the predetermined value TH3 and the change in the acceleration energy AE value is equal to or greater than a predetermined value, it is determined that the user is in an awake state (S11). In FIG. 4, it is determined that the user is in a sleep state (S7, S10) except when it is determined that the user is in an awake state (S5, S11).

As described above, the process in FIG. 4 is executed at a predetermined period, for example, at one-second intervals and information on the determination result is stored in the RAM 23 as an estimation result.

Figure 9:
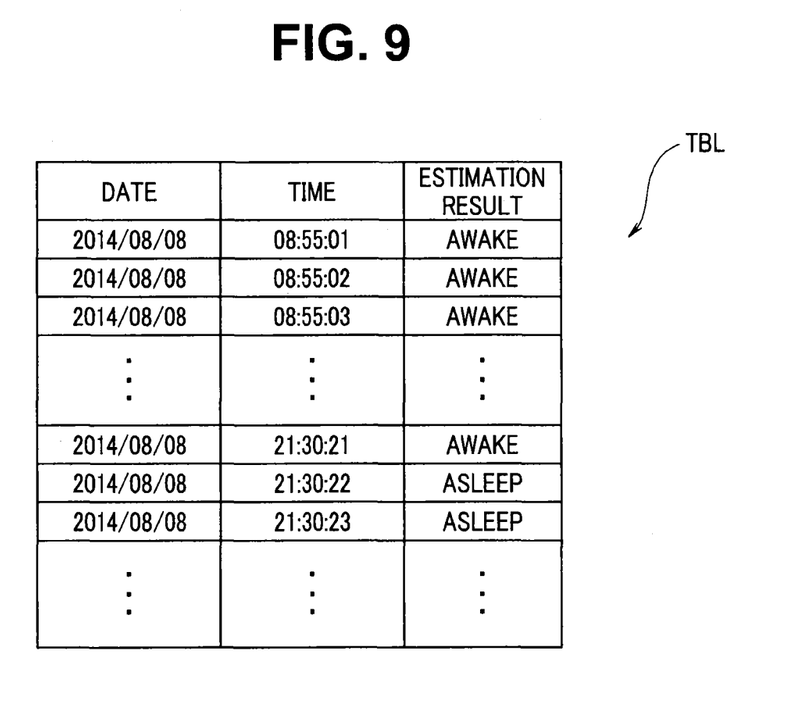
FIG. 9 is a diagram illustrating an example of a sleep/awake estimation information table TBL stored in a RAM 23 according to the embodiment.

FIG. 9 is a diagram illustrating an example of a sleep/awake estimation information table TBL stored in the RAM 23. As shown in FIG. 9, the sleep/awake estimation information table TBL includes data such as dates, times and estimation results.

When the CPU 21 determines an awake state or a sleep state through the process in FIG. 4, the CPU 21 additionally records the determination result together with information on the date and time of the clock section 24 in the sleep/awake estimation information table TBL of the RAM 23 as the estimation result.

Thus, the RAM 23 constitutes a sleep/awake state storage section configured to record information on the user's sleep state and awake state.

The CPU 21 transmits the information on the sleep/awake estimation information table TBL from the radio communication section 25 to the smartphone 2 at predetermined timing. The predetermined timing may be timing in a preset time period in the activity meter 1 or timing of a transmission request from the smartphone 2.

Thus, the radio communication section 25 constitutes an information transmitting section configured to transmit information on a sleep state and an awake state stored in the RAM 23.

The smartphone 2 may display data of the estimation result of the received sleep/awake estimation information table TBL on the display section 2a as is or in a table or graph or the like, but may also correct the received estimation result and display it on the display section 2a in a table or graph or the like.

For example, an application program of the smartphone 2 can show data of the estimation result of the sleep/awake estimation information table TBL in a table format or in a graph.

The data of the estimation result of the sleep/awake estimation information table TBL is, for example, per-second data and is generated at short time intervals. For this reason, the estimation result may contain errors.

Figure 10:
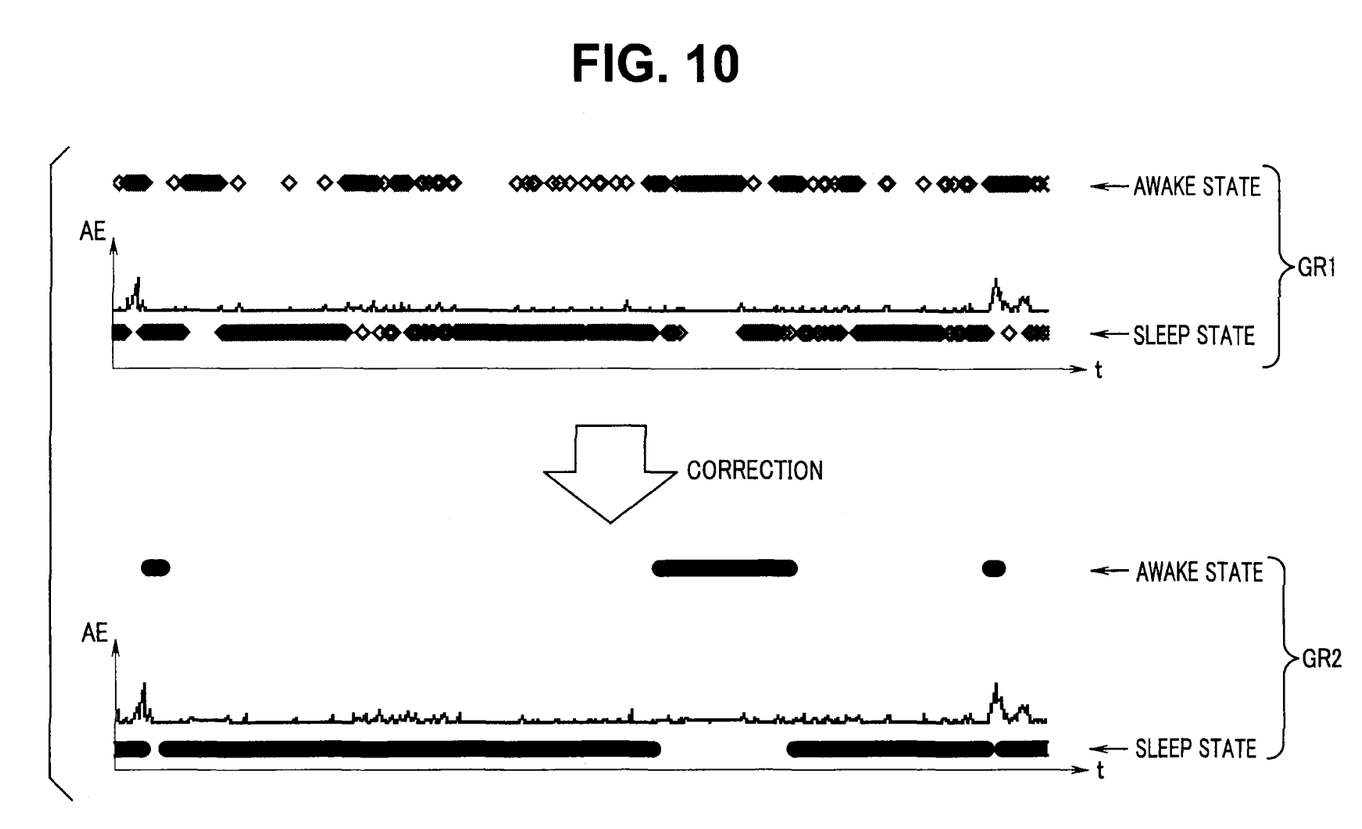
FIG. 10 is a graph of estimation results illustrating a situation in which errors are included in the estimation result according to the embodiment.

FIG. 10 is a graph of the estimation result illustrating a situation in which the estimation result contains errors.

In a graph GR1 in FIG. 10, the horizontal axis denotes a time t and shows a change in a determination result of an awake state and a sleep state transmitted from the activity meter 1 at each time. On the top row in FIG. 10, points (shown by rhombuses) indicating determinations as awake state are plotted, from which it is not possible to clearly distinguish between the sleep state and the awake state.

Thus, for example, the estimation result of the activity meter 1 may be corrected by a majority decision of adopting more numerous determination results within a predetermined time period before and after a certain time as the determination results so as to determine the sleep state and the awake state at that time.

Figure 11:
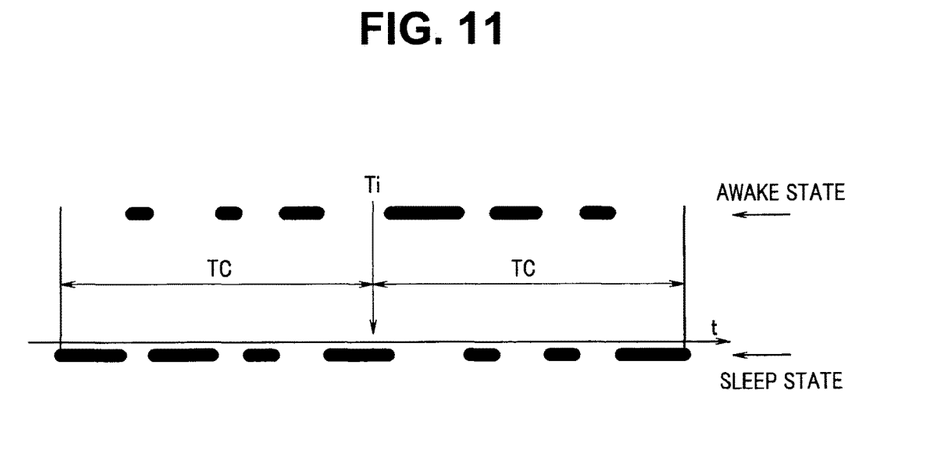
FIG. 11 is a diagram for describing an estimation result correction method in the smartphone 2 according to the embodiment.

FIG. 11 is a diagram for describing an estimation result correction method in the smartphone 2. As shown in FIG. 11, regarding a determination result at a target time Ti to be determined, the number of estimation results determined as a sleep state is compared with the number of estimation results determined as an awake state based on determination results (shown by black circles) of a TC period before and after the time Ti, and the more numerous determination results are assumed to be the determination results at the target time Ti.

A graph GR2 in FIG. 10 is a graph of an estimation result corrected using the method in FIG. 11. From the graph GR2, it is possible to clearly distinguish between the sleep state and the awake state.

Furthermore, as the corrected estimation result, a start time and an end time of a sleep state, and a start time and an end time of an awake state may be displayed on the display section 2a of the smartphone 2 in a table format.

Therefore, the smartphone 2 corrects information on the sleep/awake estimation result so as to remove errors, and can thereby more accurately determine the user's awake state and sleep state and record the determination result as data.

As described above, according to the aforementioned embodiment, it is possible to provide an activity meter which prevents, even when the activity meter is removed from the user and left unattached, an erroneous decision that the user is in a sleep state.

Moreover, it is possible to provide an activity meter that prevents, even when the user moves his/her body during a sleep, a misjudgment that the user is in an awake state.

Note that according to the aforementioned embodiment, the process in FIG. 4 is implemented by a software program which is executed by the CPU 21, but the process may be implemented also by a hardware circuit.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An activity meter attachable to a target person whose activity amount is measured, comprising:
    an acceleration sensor configured to detect acceleration in at least three axis directions;
    an acceleration energy detection section configured to detect acceleration energy based on an acceleration signal of the acceleration sensor;
    a first determining section configured to determine removal of the activity meter from the target person based on whether the acceleration energy detected by the acceleration enemy detection section is equal to or less than a first predetermined value and an acceleration component in a direction of gravity in the acceleration signal of the acceleration sensor exceeds a second predetermined value;

a second determining section configured to detect whether the acceleration energy is equal to or greater than a third predetermined value, and to detect whether a change in the acceleration energy is equal to or less than a fourth predetermined value when the acceleration energy is equal to or greater than the third predetermined value; and a control section configured to:
  detect that the target person is in an awake state, when the first determining section determines that the activity meter is removed from the target person,
  detect that the target person is in a sleep state, when the second determining section determines that the acceleration energy is not equal to or greater than the third predetermined value in a case where the first determining section determines that the activity meter is not removed from the target person,
  determine that the target person is in the sleep state when the second determining section determines that the acceleration energy is equal to or greater than the third predetermined value and the change in the acceleration energy is equal to or less than the fourth predetermined value in the case where the first determining section determines that the activity meter is not removed from the target person, and
  determine that the target person is in the awake state when the second determining section determines that the acceleration energy is equal to or greater than the third predetermined value and the change in the acceleration energy is not equal to or less than the fourth predetermined value in the case where the first determining section determines that the activity meter is not removed from the target person.

2. The activity meter according to claim 1, further comprising a sleep/awake state storage section configured to record information on the sleep state and the awake state.

3. The activity meter according to claim 2, further comprising an information transmitting section configured to transmit information on the sleep state and the awake state stored in the sleep/awake state storage section.

4. A sleep/awake state recording system comprising:
an activity meter attachable to a target person whose activity amount is measured; and
a terminal communicable with the activity meter,
wherein the activity meter includes:
  an acceleration sensor configured to detect acceleration in at least three axis directions;
  an acceleration energy detection section configured to detect acceleration energy based on an acceleration signal of the acceleration sensor;
  a first determining section configured to determine removal of the activity meter from the target person based on whether the acceleration energy detected by the acceleration energy detection section is equal to or less than a first predetermined value and an acceleration component in a direction of gravity in the acceleration signal of the acceleration sensor exceeds a second predetermined value;
  a second determining section configured to detect whether the acceleration energy is equal to or greater than a third predetermined value, and to detect whether a change in the acceleration energy is equal to or less than a fourth predetermined value when the acceleration energy is equal to or greater than the third predetermined value,
  a control section configured to:
    detect that the target person is in an awake state, when the first determining section determines that the activity meter is removed from the target person,
    detect that the target person is in a sleep state, when the second determining section determines that the acceleration energy is not equal to or greater than the third predetermined value in a case where the first determining section determines that the activity meter is not removed from the target person,
    determine that the target person is in the sleep state when the second determining section determines that the acceleration energy is equal to or greater than the third predetermined value and the change in the acceleration energy is equal to or less than the fourth predetermined value in the case where the first determining section determines that the activity meter is not removed from the target person, and
    determine that the target person is in the awake state when the second determining section determines that the acceleration energy is equal to or greater than the third predetermined value and the change in the acceleration energy is not equal to or less than the fourth predetermined value in the case where the first determining section determines that the activity meter is not removed from the target person;
  a sleep/awake state storage section configured to record information on the sleep state and the awake state; and
  an information transmitting section configured to transmit information on the sleep state and the awake state stored in the sleep/awake state storage section, and
wherein the terminal includes:
  a correction section configured to correct the information on the sleep state and the awake state received from the activity meter; and
  a storage section configured to store the corrected information.

* * * * *

UNITED STATES PATENT AND TRADEMARK OFFICE
CERTIFICATE OF CORRECTION

PATENT NO. : 9,901,291 B2  
APPLICATION NO. : 14/800071  
DATED : February 27, 2018  
INVENTOR(S) : Tomoko Murakami et al.

Page 1 of 1

It is certified that error appears in the above-identified patent and that said Letters Patent is hereby corrected as shown below:

In the Claims

Column 10, Line 63, change "enemy" to "energy"

Signed and Sealed this  
Fourth Day of June, 2019

Andrei Iancu  
*Director of the United States Patent and Trademark Office*